(12) United States Patent
Forsberg et al.

(10) Patent No.: US 11,317,888 B2
(45) Date of Patent: May 3, 2022

(54) NON-INVASIVE METHOD FOR PRESSURE MEASUREMENT

(71) Applicants: THOMAS JEFFERSON UNIVERSITY, Philadelphia, PA (US); GE PRECISION HEALTHCARE LLC, Milwaukee, WI (US)

(72) Inventors: Flemming Forsberg, Lafayette Hill, PA (US); David Mills, Niskayuna, NY (US); John R. Eisenbrey, Philadelphia, PA (US); Kirk Wallace, Niskayuna, NY (US); Ipshita Gupta, Noida (IN)

(73) Assignees: THOMAS JEFFERSON UNIVERSITY, Philadelphia, PA (US); GE PRECISION HEALTHCARE LLC, Milwaukee, WI (US)

( * ) Notice: Subject to any disclaimer, the term of this patent is extended or adjusted under 35 U.S.C. 154(b) by 394 days.

(21) Appl. No.: 16/341,334

(22) PCT Filed: Oct. 11, 2017

(86) PCT No.: PCT/US2017/056154
§ 371 (c)(1),
(2) Date: Apr. 11, 2019

(87) PCT Pub. No.: WO2018/071551
PCT Pub. Date: Apr. 19, 2018

(65) Prior Publication Data
US 2020/0046313 A1  Feb. 13, 2020

Related U.S. Application Data

(60) Provisional application No. 62/406,797, filed on Oct. 11, 2016.

(51) Int. Cl.
*A61B 8/04* (2006.01)
*A61B 8/08* (2006.01)
*A61K 49/22* (2006.01)

(52) U.S. Cl.
CPC .............. *A61B 8/04* (2013.01); *A61B 8/481* (2013.01); *A61B 8/5223* (2013.01); *A61K 49/223* (2013.01)

(58) Field of Classification Search
CPC ......... A61B 8/04; A61B 8/481; A61B 8/5223; A61K 49/223; G16H 50/30
See application file for complete search history.

(56) References Cited

U.S. PATENT DOCUMENTS 5,552,133 A  9/1996  Lambert et al.
2001/0021808 A1* 9/2001  Shi ........................ A61B 8/481
                                                              600/438

FOREIGN PATENT DOCUMENTS

WO  2014001297 A2  1/2014

OTHER PUBLICATIONS

Baigi, E., et al., "Subharmonic Emissions from Microbubbles: Effect of the Driving Pulse Shape", IEEE Transactions on Ultrasonics, Ferroelectrics, and Frequency Control, vol. 53, No. 11, pp. 2174-2182, 2006.

(Continued)

*Primary Examiner* — Peter Luong
(74) *Attorney, Agent, or Firm* — Cozen O'Connor

(57) ABSTRACT

The present invention relates to the use of contrast-enhanced ultrasound using microbubble-based ultrasound contrast agents to accomplish noninvasive subharmonic aided pressure estimation (SHAPE) in a region of interest (ROI) of a subject. The method of the invention provides a non-invasive, direct, and accurate method for pressure estimation.

31 Claims, 5 Drawing Sheets

(56) References Cited

OTHER PUBLICATIONS

Daeichin, V., et al., "Subharmonic, Non-linear Fundamental and Ultraharmonic Imaging of Microbubble Contrast at High Frequencies", Ultrasound in Medicine and Biology, vol. 41, No. 2, pp. 486-497, 2015.

Dave, J.K., et al., "Noninvasive estimation of dynamic pressures in vitro and in vivo using the subharmonic response from microbubbles", IEEE Transactions on Ultrasonics, Ferroelectrics, and Frequency Control. vol. 58, No. 10, pp. 2056-2066, 2011.

Dave, J.K., et al., "Investigating the efficacy of subharmonic aided pressure estimation for portal vein pressures and portal hypertension monitoring", Ultrasound in Medicine and Biology, vol. 38, No. 10, pp. 1784-1798, 2012.

Dave, J.K., et al., "Subharmonic microbubble emissions for noninvasevely tracking right ventricular pressures", American Journal of Physiology: Heart and Circulatory Physiology, vol. 303, No. 1, pp. H126-H132, 2012.

Dave, J.K., et al., "Noninvasive LV pressure estimation using subharmonic emissions from microbubbles", JACC Cardiovascular Imaging, vol. 5, No. 1, pp. 87-92, 2012.

Dave, J.K., et al., "Acute Portal Hypertension Models in Dogs: Low- and High-Flow Approaches", Comparative Medicine, vol. 62, No. 5, pp. 419-426, 2012.

Dave, J.K., et al., "On the implementation of an automated acoustic output optimization algorithm for subharmonic aided pressure estimation", Ultrasonics, vol. 53, No. 4, pp. 880-888, 2013.

Eisenbrey, J.R., et al., "Simultaneous grayscale and subharmonic ultrasound imaging on a modified commercial scanner", Ultrasonics, vol. 51, No. 8, pp. 890-897, 2011.

Eisenbrey, J.R., et al., "Chronic Liver Disease: Noninvasive Subharmonic Aided Pressure Estimation of Hepatic Venous Pressure Gradient", Radiology, vol. 268, No. 2, pp. 581-588, 2013.

Forsberg, F., et al., "Subharmonic imaging of contrast agents", Ultrasonics, vol. 38 Nos. 1-8, pp. 93-98, 2000.

Forsberg, F., et al., "In vivo pressure estimation using subharmonic contrast microbubble signals: proof of concept", IEEE Transactions on Ultrasonics, Ferroelectrics, and Frequency Control, vol. 52, No. 4, pp. 581-583, 2005.

Halldorsdottir, V.G., et al., "Subharmonic Contrast Microbubble Signals for Noninvasive Pressure Estimation under Static and Dynamic Flow Conditions", Ultrasonic Imaging, vol. 33, No. 3, pp. 153-164, 2011.

Halpern, E.J., et al., "Contrast-enhanced US of the Prostate with Sonazoid: Comparison with Whole-Mount Prostatectomy Specimens in 12 Patients", Radiology, vol. 222, No. 2, pp. 361-366, 2002.

International Search Report issued in International Application No. PCT/US2017/056154 dated Feb. 27, 2018.

Lauterborn, W., "Numerical investigation of nonlinear oscillations of gas bubbles in liquids", The Journal of the Acoustical Society of America, vol. 59, No. 2, pp. 283-293, 1976.

Liu, S., et al., "Ambient Pressure Evaluation through Sub-Harmonic Response of Chirp-Sonicated Microbubbles", Ultrasound in Medicine and Biology, vol. 43, No. 1, pp. 332-340, 2017.

Prosperetti, A., "Nonlinear oscillations of gas bubbles in liquids—Transient solutions and the connection between subharmonic signal and cavitation", The Journal of the Acoustical Society of America, vol. 57, No. 4, pp. 810-821, 1975.

Prosperetti, A., The Journal of the Acoustical Society of America, vol. 61, pp. 11-16, 1994.

Shankar, P.M., et al., "Subharmonic backscattering from ultrasound contrast agents", The Journal of the Acoustical Society of America, vol. 106, No. 4, pp. 2104-2110, 1999.

Shekhar, H., et al., "Improving the sensitivity of high-frequency subharmonic imaging with coded ecitation: A feasibility study", Medical Physics, vol. 39, No. 4, pp. 2049-2060, 2012.

Shi, W.T., et al., "Subharmonic Imaging with Microbubble Contrast Agents: Initial Results", Ultrasonic Imaging, vol. 21, No. 2, pp. 79-94, 1999.

Shi, W.T., et al., "Pressure dependence of subharmonic signals from contrast microbubbles", Ultrasound in Medicine and Biology, vol. 25, No. 2, pp. 275-283, 1999.

Stride, E.P., et al., "Cavitation and contrast: the use of bubbles in ultrasound imaging and therapy", Proceedings of the Institution of Mechanical Engineers Part H—Journal of Engineering in Medicine, vol. 224(H2), pp. 171-191, 2010.

Zhang, D., et al., "Enhancement of subharmonic emission from encapsulated microbubbles by using a chirp excitation technique", Phys. Med. Biol., vol. 52, No. 18, pp. 5531-5544, 2007.

* cited by examiner

| | Description | Input Waveform | Hydrophone |
|---|---|---|---|
| A | Square Wave |  |  |
| B | Gaussian Windowed Square Wave |  |  |
| C | Sine Wave |  |  |
| D | Binomial Filtered Square Wave |  |  |
| E | Gaussian Windowed Binomial Filtered Square |  |  |
| F | Gaussian Windowed Binomial Filtered Square 90° shift |  |  |
| G | Chirp Up |  |  |
| H | Chirp Down |  |  |

FIG. 2 – continued
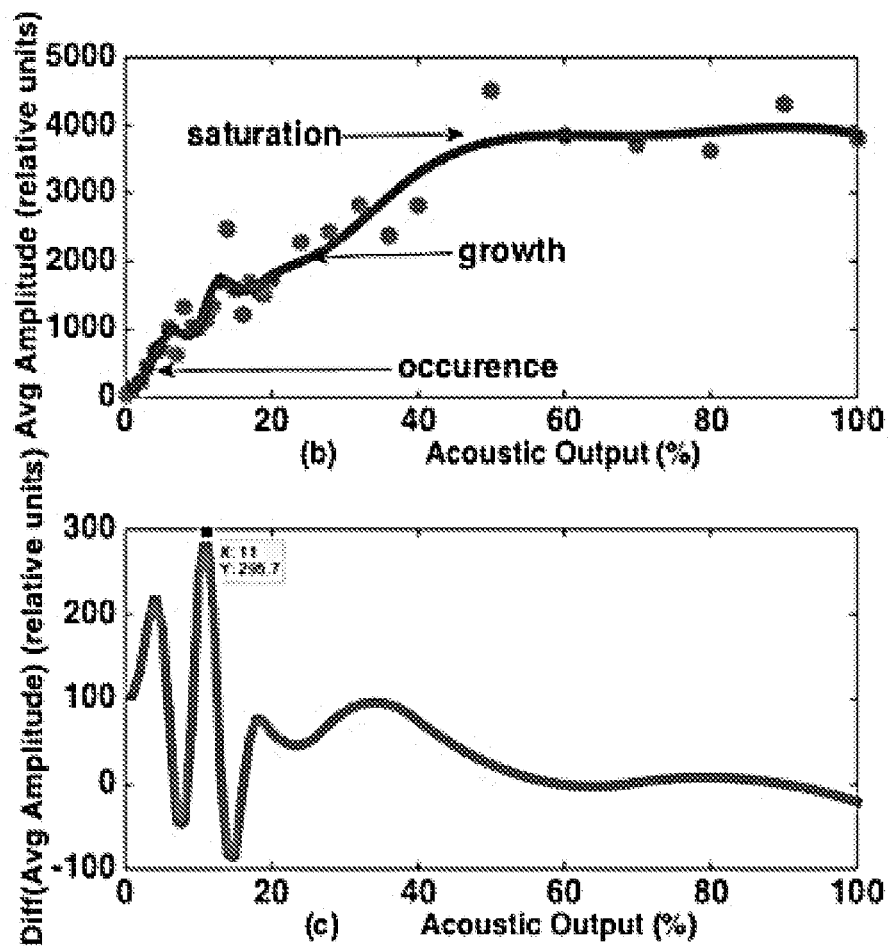

NON-INVASIVE METHOD FOR PRESSURE MEASUREMENT

CROSS REFERENCE TO RELATED APPLICATIONS

This is an United States National Stage application of International Patent Application No. PCT/US2017/056154, filed Oct. 11, 2017, published as WO 2018/071551 on Apr. 19, 2018, which claims priority to U.S. Provisional Patent Application No. 62/406,797, filed Oct. 11, 2016, the entirety of each of which is incorporated herein by reference.

GOVERNMENT SUPPORT

This invention was made with government support under DK098526 awarded by the National Institutes of Health. The government has certain rights in the invention.

FIELD OF INVENTION

The present invention relates to a method to measure pressure in a region of interest (ROI) in a subject. In particular, the method of the invention is a contrast-enhanced ultrasound procedure that makes use of a microbubble ultrasound contrast agent (UCA) and the property of compressibility which enables the microbubbles to vary significantly in size in response to changes in pressure.

BACKGROUND OF THE INVENTION

Microbubble ultrasound contrast agents ("UCAs") are encapsulated microbubbles that oscillate nonlinearly within the pressure field caused by ultrasound pulses at higher incident pressures (>200 kPa). The gas within these microbubbles has a different compressibility than blood leading to an acoustic impedance mismatch between the two, and an increase in scattering; hence, the microbubbles enhance the backscattered ultrasound signal (Stride & Coussios 2010 Proceedings of the Institution of Mechanical Engineers Part H-Journal of Engineering in Medicine; 224 (H2): 171-91). The UCA's nonlinear oscillations occur over a wide range of frequencies from subharmonics ($f_0/2$), and second harmonics ($2f_0$) to ultraharmonics ($3f_0/2$) of the insonation frequency as well as multiples thereof. These signals can be used to create contrast specific imaging modes, such as subharmonic imaging (SHI) as well as harmonic and superharmonic imaging (Forsberg et al. 2005 Ieee Transactions on Ultrasonics Ferroelectrics and Frequency Control; 52(4):581-3). Harmonic imaging where ultrasound is transmitted at $f_0$ and received at $2f_0$ provides for restricted bandwidth since the tissue produces significant harmonic energy and leads to reduced blood to tissue contrast. SHI transmits at double the resonant frequency and receives at half the transmit frequency i.e., $f_0/2$ (Forsberg et al., supra; Shankar et al. 1999 J Accoustical Soc Am; 106(4):2104-10). Since the surrounding tissue does not generate subharmonic response at the low power levels used, SHI has an excellent contrast-to-tissue ratio (CTR) i.e., the ratio of the mean bubble and tissue signal amplitudes. CTR values as high as 20 dB have been reported in vitro by Daechin et al. (2015 Ultrasound Med Biol; 41(2): 486-97).

A novel and innovative technique called subharmonic-aided pressure estimation (SHAPE) has been proposed (Forsberg et al., supra.; Shi et al. 1999 Ultrasound Med Biol; 25(2): 275-83). It has been established previously that there are three stages in the subharmonic signal generation from microbubbles in response to changing acoustic pressure namely occurrence, growth and saturation (Shi et al., supra). In the growth phase, the subharmonic signal amplitude has the highest sensitivity to pressure changes and an inverse linear relation with the ambient pressure (Forsberg et al., supra; Shi et al., supra). It is this stage, which is used with the SHAPE procedure to estimate ambient pressure. An in vitro study comparing five different contrast agents showed Sonazoid (GE Healthcare, Oslo Norway), to be the most sensitive for SHAPE applications having the highest gradient in subharmonic amplitude as the pressure was changed from 0 to 186 mmHg and a correlation coefficient (r) of 0.99 (Halldorsdottir et al. 2011 Ultrasonic Imaging; 33(3): 153-164).

The feasibility of using SHAPE to estimate the ambient pressures noninvasively has been confirmed (Shi et al., supra; Shi et al. 1999 Ultrasonic Imaging; 21(2): 79-94; Forsberg et al. 2000 Ultrasonics; 38(1-8): 93-98). High correlation coefficients have been reported (r=−0.98) in a static tank when pressure was varied from 0 to 186 mmHg with a slope of −0.07 dB/mmHg using a square enveloped input pulse (Halldorsdottir et al., supra). Another study analyzed the efficacy of SHAPE with Sonazoid in predicting portal hypertension in canines and showed r-values from −0.71 to −0.79 between the absolute portal vein pressure and subharmonic signal amplitude (Dave et al. 2012 Ultrasound Med Biol; 38(10): 1784-1798). A pilot study of SHAPE in 45 patients with chronic liver disease indicated SHAPE might become a useful tool for screening patients with portal hypertension and those at risk for variceal bleeding. The SHAPE gradient and hepatic venous pressure gradient (HVPG) values showed a linear correlation of 0.82 for subjects with a HVPG >10 mmHg and 0.97 for patients with a HVPG >12 mmHg (Eisenbrey et al. 2013 Radiology; 268(2): 581-588).

Biagi et al. (2006 Ieee Transactions on Ultrasonics Ferroelectrics and Frequency Control; 53(11): 2174-2182) investigated the subharmonic response of Sonovue to different shaped pulses. They proved that the initial envelope of the pulse has a strong effect on the subharmonic amplitude. Zhang et al. (2007 Phys Med Biol; 52(18): 5531-5544) showed that chirp excitation with a center frequency of 5 MHz enhances the subharmonic emission of encapsulated microbubbles. Another study by Shekhar and Doyley (2012 Med Phys; 39(4): 2049-2060) used rectangular windowed coded chirp excitation for intra vascular ultrasound imaging. They concluded that the chirp pulse with a higher bandwidth gave a 5.7 dB higher ratio of subharmonic to fundamental response amplitude than a narrowband sine wave. They also achieved a higher axial resolution with the broadband chirp pulse.

SUMMARY OF THE INVENTION

The present invention relates to a method for obtaining a pressure measurement in at least one region of interest (ROI) in a subject wherein said method comprises: (i) administering a diagnostically effective amount of a microbubble ultrasound contrast agent (UCA) to said subject; (ii) allowing said UCA to accumulate in said subject; (iii) transmitting an ultrasonic wave to said ROI in said subject wherein said ultrasonic wave is a broadband wave; (iv) optimising the acoustic power for said ultrasonic wave; (v) receiving an ultrasonic echo generated by reflecting the ultrasonic wave transmitted in step (iii) from said ROI thereby acquiring a detection signal; (vi) extracting a sub-harmonic component from the ultrasonic echo based on the detection signal; and (vii) using the inverse linear relationship between the subharmonic signal amplitude and the ambient pressure to obtain said pressure measurement.

The method of the invention using this particular waveform provides a surprising improvement to the existing SHAPE technique where a square wave was used and should make SHAPE more sensitive for the in vivo measurement of pressure.

A further method is directed towards a method for obtaining a pressure measurement in at least one region of interest (ROI) in a mammal wherein said method comprises: (i) intravenously administering a diagnostically effective amount of a microbubble ultrasound contrast agent (UCA) to said subject; (ii) allowing said UCA to accumulate in said subject; (iii) transmitting an ultrasonic wave in the form of a Gaussian windowed binomial filtered square wave to said ROI in said subject wherein said ultrasonic wave is a broadband wave; (iv) optimising the acoustic power for said ultrasonic wave; (v) receiving an ultrasonic echo generated by reflecting the ultrasonic wave transmitted in step (iii) from said ROI thereby acquiring a detection signal; (vi) extracting a sub-harmonic component from the ultrasonic echo based on the detection signal; and (vii) using the inverse linear relationship between the subharmonic signal amplitude and the ambient pressure to obtain said pressure measurement.

DETAILED DESCRIPTION OF THE PREFERRED EMBODIMENTS

Figure 1:
FIG. 1: Waveform settings implemented for SHI and SHAPE investigation.
Figure 1:
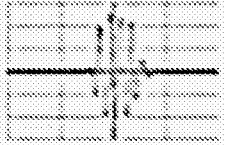
Figure 1:
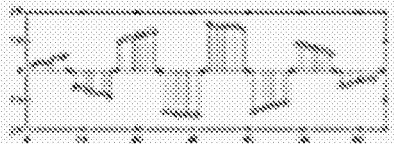
Figure 1:
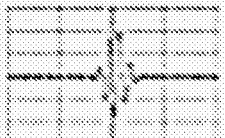
Figure 1:
Figure 1:
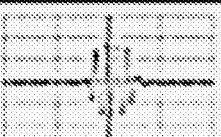
Figure 1:
Figure 1:
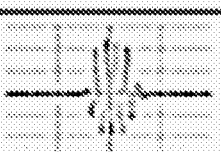
Figure 1:
Figure 1:
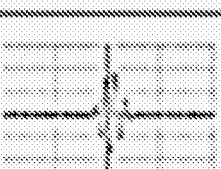
Figure 1:
Figure 1:
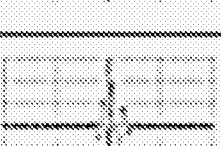
Figure 1:
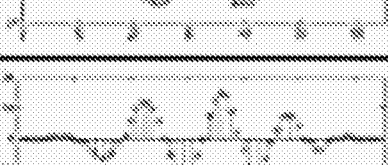
Figure 1:
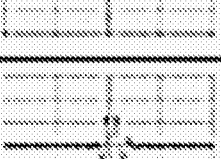
Figure 1:
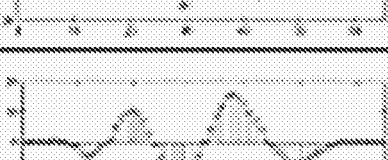
Figure 1:
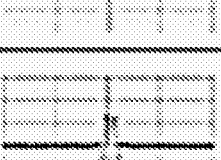

To more clearly and concisely describe and point out the subject matter of the claimed invention, definitions are provided herein below for specific terms used throughout the present specification and claims. Any exemplification of specific terms herein should be considered as a non-limiting example.

List of Abbreviations Used in the Examples

DICOM digital imaging and communications in medicine
MIP maximum intensity projection
RF radiofrequency
ROI region of interest
SHAPE subharmonic-aided pressure estimation
SHI subharmonic imaging The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "region of interest" (ROI) can be understood to be a particular anatomical location within the subject of the invention. Alternatively, as the method of the invention includes generation of an image, the ROI can be regarded as an area on a digital image that circumscribes a desired anatomical location.

The "subject" of the invention can be any human or animal subject. In one embodiment the subject of the invention is a mammal. In one embodiment said subject is an intact mammalian body in vivo. In another embodiment, the subject of the invention is a human.

"Administering" the UCA is preferably carried out parenterally. In one embodiment the UCA is administered intravenously. The intravenous route represents an efficient way to deliver the UCA throughout the body of the subject. Furthermore, intravenous administration does not represent a substantial physical intervention or a substantial health risk. In one embodiment the UCA is administered as a pharmaceutical composition.

A "microbubble contrast agent" (UCA) is a suspension of small gas bubbles, used to enhance ultrasound contrast. Each of the bubbles (referred to as microbubbles) comprises a gas encapsulated in a shell. Known commercially-available UCAs include Optison and Sonazoid (both from GE Healthcare), SonoVue and Lumason (from Bracco), Levovist (by Schering) and Definity and Luminity (from Lantheus Medical Imaging). Optison consists of microspheres of protein-type A microspheres that contain perflutren. Sonazoid consists of microspheres with an outer lipid shell that encapsulates perfluorobutane gas. Definity and Luminty consist of microspheres with an outer lipid shell that encapsulates perflutren. SonoVue and Lumason consist of microspheres with an outer lipid shell that encapsulates sulfur hexafluoride gas. Levovist has a galactose/palmitic acid shell surrounding air.

The term "transmitting an ultrasonic wave" refers to the process by which a wave typically having a frequency in the range 2 to 20 MHz is generated and sent into a body. The ultrasonic wave is generated by a transducer that can convert AC into ultrasound. A typical transducer as will be known to those of skill in the art is either a piezoelectric transducer or a capacitive transducer. Piezoelectric crystals change size and shape when a voltage is applied; AC voltage makes them oscillate at the same frequency and produce ultrasonic sound. Capacitive transducers use electrostatic fields between a conductive diaphragm and a backing plate.

The term "receiving an ultrasonic echo" refers to the process whereby transmitted ultrasound waves that are reflected back from surfaces encountered the body are picked up by the transducer as a "detection signal".

The term "sub-harmonic component" refers to a particular oscillation of the microbubbles in the UCA. There are many interesting bubble oscillations which span the range of possible frequency emissions from subharmonics (as well as ultraharmonics) through higher harmonics (Lauterborn 1976 J Acoust Soc Am; 59: 283-293). Subharmonic oscillation of a free bubble occurs only when the exciting acoustic signal exceeds a certain threshold level (as described for example by Prosperetti 1975 J Acoust Soc Am; 57: 810-821; Prosperetti 1994 J Acoust Soc Am; 61: 11-16 and Leighton, T. G., The Acoustic Bubble. Academic Press, London, Great Britain, 1994).

The signal amplitude of the sub-harmonic component is calculated using software that fits a logistic curve to the data and selects an inflection point as the optimized power or point of greatest SHAPE sensitivity.

The "inverse linear relationship" between the subharmonic signal amplitude and the ambient pressure is established by generation of a standard curve onto which the obtained sub-harmonic signal amplitude is applied.

As described hereinabove, UCAs are well known in the art of in vivo imaging. Commercially-available UCAs are typically produced by shaking or sonicating a liquid containing a membrane-forming material in the presence of a suitable gas or gas mixture. Other processes include spray drying. U.S. Pat. No. 5,552,133 describes a process for making encapsulated gas microspheres comprising a heat-denaturable protein encapsulating a gas, using a colloid mill. An aqueous solution of a heat-denaturable protein is combined with a gas, and is mixed by applying mechanical shear forces to the mixture to form a suspension of gas microbubbles, wherein the protein becomes denatured and deposited at the gas-solution interface. WO2014001297 describes a process where an aqueous solution of a heat-denaturable protein is combined with a gas, and these are mixed mechanically using high shear forces. When preparing microbubbles it is important to have a robust process that repeatedly provides a product according to product specifications. Desirably the microbubbles produced will have a narrow size distribution about the desired microbubble size, generally 1 to 7 μm, e.g., including the ranges, 2-6 and 3-5 μm. The percentage of large microbubbles, such as above 7 μm should be minimal and well limited. Microbubble size can be precisely controlled by adjusting the gas and liquid flow rates.

In one embodiment, disclosed is a method for obtaining a pressure measurement in at least one region of interest (ROI) in a subject wherein said method comprises: (i) administering a diagnostically effective amount of a microbubble ultrasound contrast agent (UCA) to said subject; (ii) allowing said UCA to accumulate in said subject; (iii) transmitting an ultrasonic wave to said ROI in said subject wherein said ultrasonic wave is a broadband wave; (iv) optimising the acoustic power for said ultrasonic wave; (v) receiving an ultrasonic echo generated by reflecting the ultrasonic wave transmitted in step (iii) from said ROI thereby acquiring a detection signal; (vi) extracting a sub-harmonic component from the ultrasonic echo based on the detection signal; and (vii) using the inverse linear relationship between the sub-harmonic signal amplitude and the ambient pressure to obtain said pressure measurement.

In one embodiment of the method of the invention said subject is a mammal.

In one embodiment of the method of the invention said mammal is a human.

In one embodiment of the method of the invention said administering is intravenous.

In one embodiment of the method of the invention administering is an infusion. For example a vial of UCA can be dissolved in saline and dripped into a patient at a defined rate, e.g., dissolve a vial of Definity in 50 mL saline and drip it in.

In one embodiment of the method of the invention said administering is a co-infusion with saline. A non-limiting exemplary co-infusion could be around 100-200 mL/hr saline plus 0.10-0.20 mL/hr UCA, or 100-150 mL/hr saline plus 0.15-0.20 mL/hr UCA, e.g. for Sonazoid a non-limiting infusion could be 120 mL/hr saline in conjunction with 0.18 mL/hr Sonazoid.

In one embodiment of the method of the invention said UCA comprises microbubbles each of which comprises a gas enclosed by a stabilising shell.

In one embodiment of the method of the invention said gas has a different compressibility compared to the blood of said subject.

In one embodiment of the method of the invention said gas is a high-density, high-molecular weight gas that exhibits low solubility.

In one embodiment of the method of the invention said gas is selected from the group comprising perflutren, perfluorobutane (PFB), octafluoropropane or sulfur hexafluoride.

In one embodiment of the method of the invention said stabilising shell comprises a protein, lipid or polymer.

In one embodiment of the method of the invention said stabilising shell comprises a protein.

In one embodiment of the method of the invention said protein is albumin.

In one embodiment of the method of the invention said stabilising shell comprises a lipid.

In one embodiment of the method of the invention said lipid is a phospholipid.

In one embodiment of the method of the invention said phospholipid is phosphatidyl serine (PS).

In one embodiment of the method of the invention said phospholipid is hydrogenated egg phosphatidyl serine (HEPS).

In one embodiment of the method of the invention said stabilising shell comprises a polymer.

In one embodiment of the method of the invention said polymer is an aliphatic polyester based on lactic acid (PLA) and lactic/glycolic acid (PLGA).

In one embodiment of the method of the invention said polymer is alginate.

In one embodiment of the method of the invention said UCA is Sonazoid.

In one embodiment of the method of the invention said UCA is SonoVue.

In one embodiment of the method of the invention said ultrasonic wave is a Gaussian windowed pulse.

In one embodiment of the method of the invention said Gaussian windowed pulse is selected from the group comprising a Gausian windowed square wave, a Gaussian windowed binomial filtered square wave, a Gaussian windowed binomial filtered square 90° shift wave.

In one embodiment of the method of the invention said ultrasonic wave is a chirp pulse. Said chirp pulse can be a chirp up or a chirp down pulse.

The method of the present invention may be applied to a number of different ROIs in a subject's body and may be applied to obtain an absolute measurement as in the heart (i.e. blood pressure measurement in left or right ventricle) or a gradient/differential measurement e.g. the portal vein vs. hepatic vein or a diseased tissue vs. healthy tissue.

In one embodiment of the method of the invention said ROI comprises the portal vein of said subject.

In one embodiment of the method of the invention said ROI comprises the portal vein and the hepatic vein of said subject.

In one embodiment of the method of the invention said ROI comprises a heart cavity of said subject.

In one embodiment of the method of the invention said heart cavity is a ventricle.

In one embodiment of the method of the invention said ventricle is the left ventricle.

In one embodiment of the method of the invention said ROI comprises a diseased tissue in said subject.

In one embodiment of the method of the invention said diseased tissue is one of the group comprising a malignant tumour or an atherosclerotic plaque.

In one embodiment of the method of the invention said ROI further comprises non-diseased tissue in said subject.

The UCA can be administered by either bolus or infusion. As a non-limiting example, for Sonazoid the usual dosage for an adult is 0.015 ml/kg body weight in a single administration (see Sonazoid package insert, 2014 available at http://www3.gehealthcare.co.kr/ko-kr/prodtucts/categories/contrast_media/sonazoid).

In the experimental examples described below, eight waveforms with different envelopes were optimized with respect to acoustic power at which the SHAPE study is most sensitive. The study was run with four input transmit cycles, first in vitro and then in vivo in three canines to select the waveform that achieved the best sensitivity for detecting changes in portal pressures using SHAPE. A Logiq 9 scanner (GE Healthcare, Waukesha, Wis., USA) with a 4C curvi-linear array was used to acquire 2.5 MHz radio-frequency (RF) data. Scanning was performed in dual imaging mode with B-mode imaging at 4 MHz and a SHI contrast mode transmitting at 2.5 MHz and receiving at 1.25 MHz. Sonazoid (GE Healthcare, Oslo, Norway), which is a lipid stabilized gas filled bubble of perfluorobutane, was used as the contrast agent in this study. A linear decrease in subharmonic amplitude with increased pressure was observed for all waveforms (r from −0.77 to −0.93; p<0.001) in vitro. There was a significantly higher correlation of the SHAPE gradient with changing pressures for the broadband pulses as compared to the narrowband pulses in both in vitro and in vivo results. The highest correlation was achieved with a Gaussian windowed binomial filtered square wave with an r-value of −0.95.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The examples described below relate to in vitro and in vivo experiments carried out to assess various waveforms for use in SHAPE.

Materials and Methods

A set of eight pulse waveforms for SHI and SHAPE were tested in this study. The waveforms, along with their envelopes and alphabetical naming, are shown in FIG. 1. The square wave is the current pulse used in all the previous studies conducted by the present inventors and is denoted as waveform A. A Logiq 9 scanner (GE Healthcare, Waukesha, Wis., USA) with a 4C curvi-linear array was used to acquire radio-frequency (RF) data at the focal zone depth (9 cm) at a 12 Hz framerate. Scanning was performed in dual imaging mode with B mode operating at 4 MHz and contrast SHI transmitting 4 cycle pulses at 2.5 MHz and receiving at 1.25 MHz; based on our previous SHAPE studies (Halldorsdottir et al., supra; Dave et al., 2012 Ultrasound Med Biol, supra; Dave et al. 2011 Ieee Transactions on Ultrasonics Ferroelectrics and Frequency Control; 58(1): 2056-2066; Dave et al. 2012 Am J Physiol: Heart and Circulatory Physiol; 303(1): H126-H132; Dave et al. 2012 Jacc: Cardiovasc Imaging; 5(1): 87-92; Dave et al. 2012 Comparative Medicine; 62(5): 419-426; Eisenbrey et al. 2011 Ultrasonics; 51(8): 890-897).

Data from each acquisition was saved as a DICOM file and the RF data extracted using proprietary software (GE Global Research, Niskayuna N.Y., USA). The extracted data gave both the B-mode and the subharmonic RF data, the latter of which is DC-filtered B mode data with a center frequency of 1.25 MHz and a 0.50 MHz bandwidth.

Additionally, the incident acoustic pressures from 0 to 100% were measured in vitro at the focus of the 4C transducer using a calibrated 0.5 mm needle hydrophone (Precision Acoustics, Dorchester, Dorset, UK; sensitivity of 337 mV/MPa at 2.5 MHz) using a standard water bath approach. The measured maximum incident acoustic pressures ranged from 1.0 to 1.6 MPa peak-to-peak.

In Vitro Experimental Setup

Contrast signals at hydrostatic pressures varying from 10 to 40 mmHg were measured using a 2.25 L water tank. The water tank was also equipped with an acoustic window made out of thin plastic (thickness: 1.5 mm; Halldorsdottir et al., supra). The pressure inside could be varied by injecting air through a special inlet on the back wall of the tank and was monitored by a pressure gauge (OMEGA Engineering Inc., Stamford, Conn., model DPG1000B-05G). An inlet on the top of the tank was constructed for injecting microbubbles and placing the pressure gauge. The scanner was used to acquire RF data at the optimized acoustic power associated with each individual waveform (in triplicate) for each pressure value following injection of the contrast in a 0.2 mL/L dose into saline (Isoton II; Coulter, Miami, Fla.). The mixture was kept homogenous by a magnetic stirrer. All data was acquired in triplicate.

In Vivo Experimental Setup

All animal studies were approved by the Institutional Animal Care and Use Committee of our University and conducted in accordance with the guidelines provided by the NIH. A total of three canines were fasted for 24 hours to reduce portal vein flow and thus reduce experimental variability (Wylie and Churchill-Davidson 2004 "A Practice of Anesthesia: British Journal of Anesthesia"; Arnold, London: Healy & Knight, Eds.). The canines were kept under anesthesia during the entire procedure using standard techniques. The canines were placed on a warming blanket to maintain normal body temperature. Their abdomen was shaved and covered in gel to improve the acoustic interface to the transducer.

A midline abdominal incision was created to provide access to the main portal vein. An 18-gauge catheter was placed in a forelimb vein for contrast infusion. The pressure catheter (Millar Instruments, Inc., Houston, Tex., USA) was connected to a digital oscilloscope (Model 9350 AM, LeCroy, Chestnut Ridge, N.Y., USA) through the transducer control unit (TCB 500, Millar Instruments) and then advanced through the splenic vein into the main portal vein to acquire pressure measurements simultaneously with the SHAPE study. The 4C probe was positioned transcutaneously over the portal vein. A sonographer with more than 10 years of experience performed all the scanning. A sonographer and a physician confirmed the presence of the pressure catheter in the portal vein and the patency of the portal vein using standard grayscale imaging.

An intravenous co-infusion of saline (120 ml/hour) and 0.18 mL/kg/hour of Sonazoid was employed based on prior experience (Eisenbrey et al. 2013, supra; Halpern et al. 2002 Radiology; 222(2): 361-366). All data was collected after visual verification of Sonazoid microbubbles in the portal vein.

Figure 2:
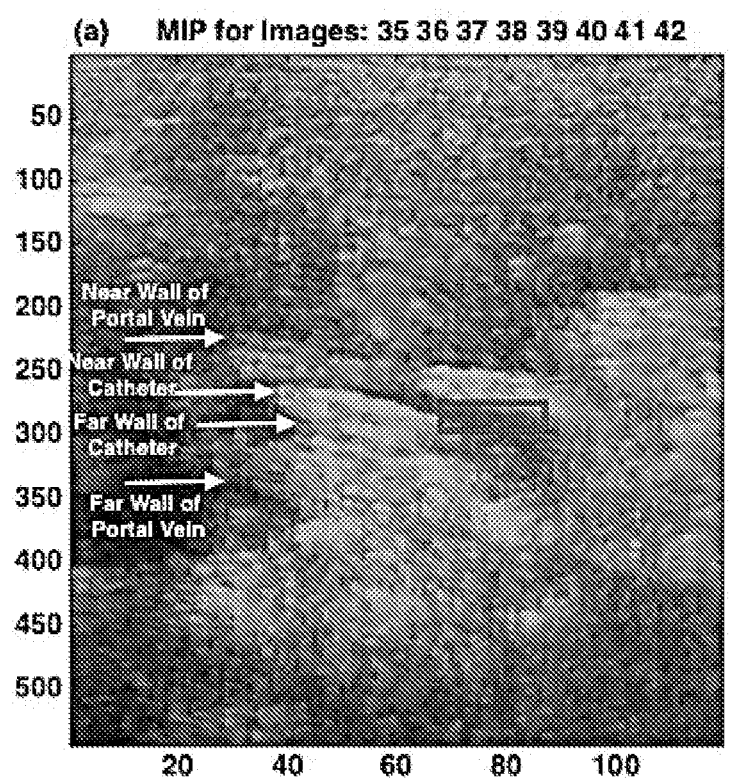
FIG. 2: Automated power optimization algorithm, [a]: Maximum Intensity Projection (MW) of SHI, the square represents the ROI selected within the portal vein; [b]: the three stages of subharmonic signal generation namely occurrence, growth and saturation with changing incident pressures from 0 to 100% of maximum acoustic pressures, [c]: y axis represents the change in subharmonic amplitude mapped from the top figure, the point represented by the highest peak is shown to have the highest SHAPE sensitivity.

The acoustic power was optimized independently for each of the 8 waveforms using the algorithm developed previously by our group (Dave et al. 2012 Ultrasound Med Biol, supra). An ROI within the portal vein was selected in the contrast image and the automated power control algorithm was initiated to determine the optimal acoustic output power for maximum SHAPE sensitivity to account for varying depth and attenuation. Briefly, the automated program acquires data for every acoustic output level, and the extracted subharmonic amplitude is plotted as a function of acoustic output. A logistic curve is fit to the data and the inflection point is selected as the optimized power, as this has been shown to be the point of greatest SHAPE sensitivity (Shi et al., 1999 Ultrasound Med Biol, supra). One such curve is shown in FIG. 2.

Cine loops were collected in triplicate for 6 seconds, before and after induction of portal hypertension by embolization of the liver microcirculation. This was done through injection of approximately 5 mL of Gelfoam (Ethicon, Somerville, N.J.) mixed with 4 to 5 mL of saline (resulting in pressure values of 10 to 30 mmHg), into the main portal vein.

Data Processing and Analysis

The RF data from each acquisition was extracted using proprietary software (GE Global Research) as described above. Regions within the portal veins previously identified by the sonographer were selected on maximum intensity projection (MIP) of B-mode images (compiled from reconstructed images from the RF data) and were fixed throughout the 6-second acquisition (approximately 27-30 frames). The subharmonic amplitude was calculated in a 0.5 MHz bandwidth around 1.25 MHz. Correlation coefficients and regression line slopes were calculated to check for the waveform with the best sensitivity and correlation with pressure. The waveform with the highest negative slope and a highly negative correlation coefficient (r) between the subharmonic amplitude and pressure was selected for further use in clinical trials. All statistical analysis was conducted using Matlab 2014b (The MathWorks, Inc, Natick, Mass., USA). Waveforms were also divided into two groups of being broadband (waveforms B, E, F, G & H) and narrowband (waveforms A, C & D) and analyzed to determine if one group performed better than the other.

Results

In Vitro

Figure 3:
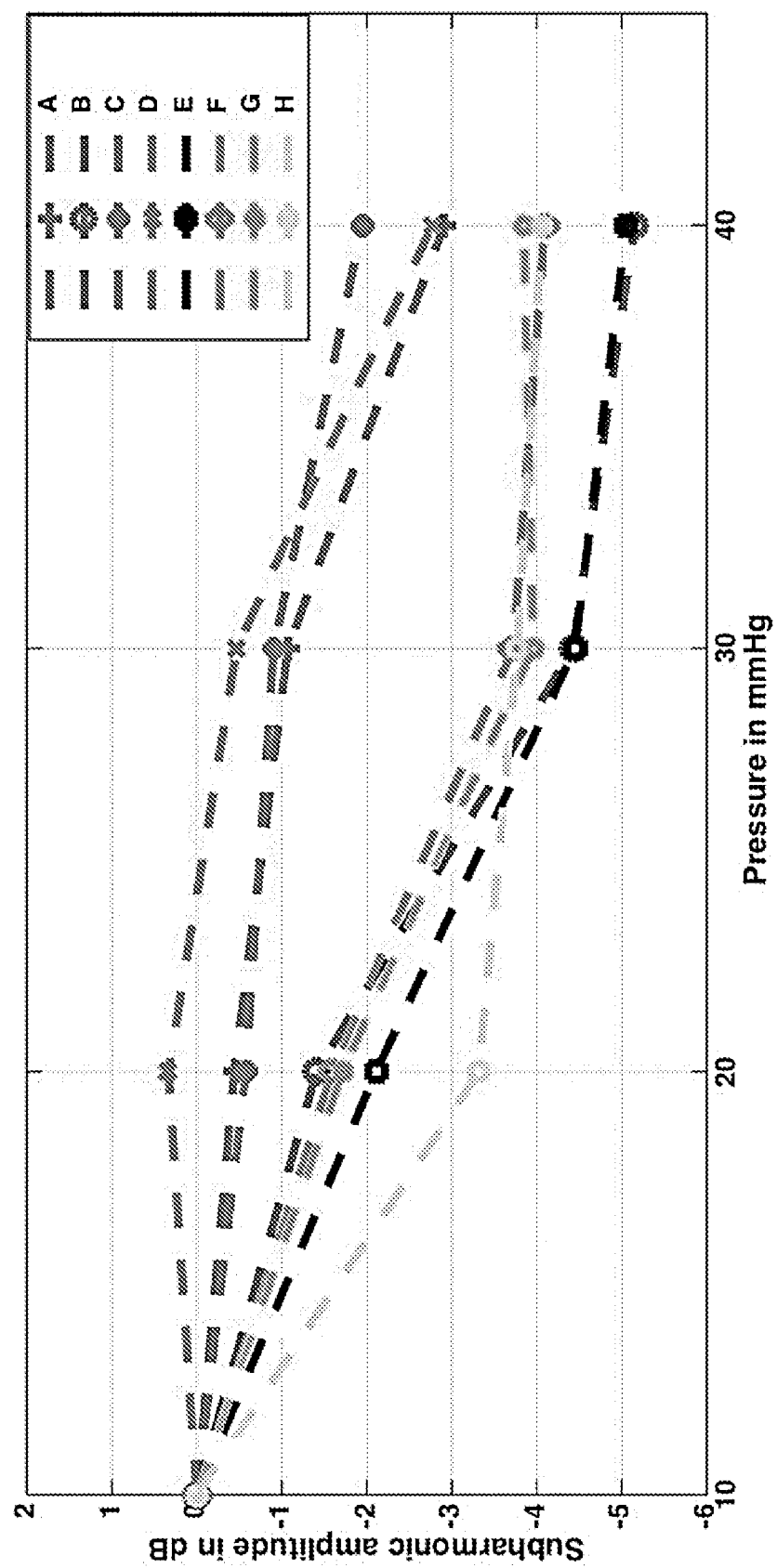
FIG. 3: In vitro setup: mean subharmonic amplitude v/s pressure for all eight pulse envelopes.

The in vitro tank data resulted in correlation values ranging from −0.77 to −0.95 between the subharmonic amplitude change and the hydrostatic pressure. All changes in subharmonic amplitude were statistically significant with increasing pressure (p<0.001). FIG. 3 shows the reduction in subharmonic amplitude as the pressure is increased in the in vitro setup. The values for the correlation coefficients and the slope between the subharmonic amplitude and pressure change for all the eight waveforms are presented in Table 1 below.

TABLE 1

Slope (between the subharmonic amplitude and ambient pressure) and r values for all eight waveforms (A-H) in vitro

|  | A | B | C | D | E | F | G | H |
|---|---|---|---|---|---|---|---|---|
| SLOPE (dB/mmHg) | −0.10 | −0.17 | −0.06 | −0.09 | −0.17 | −0.14 | −0.13 | −0.14 |
| r | −0.88 | −0.90 | −0.79 | −0.77 | −0.95 | −0.93 | −0.91 | −0.81 |

In Vivo

In the first canine, across all the eight waveforms, the normal baseline pressure was 9.9±0.0 mmHg, which increased to 39.2±0.4 mmHg post induction of hypertension. For the second canine, the baseline pressure was 9.4±0.0 mmHg and it rose to 20.0±0.8 mmHg post gelfoam injection. For the third canine, the baseline pressure was 11.2±0.8 mmHg, which increased to 34.8±1.6 mmHg post induction of hypertension.

Figure 4:
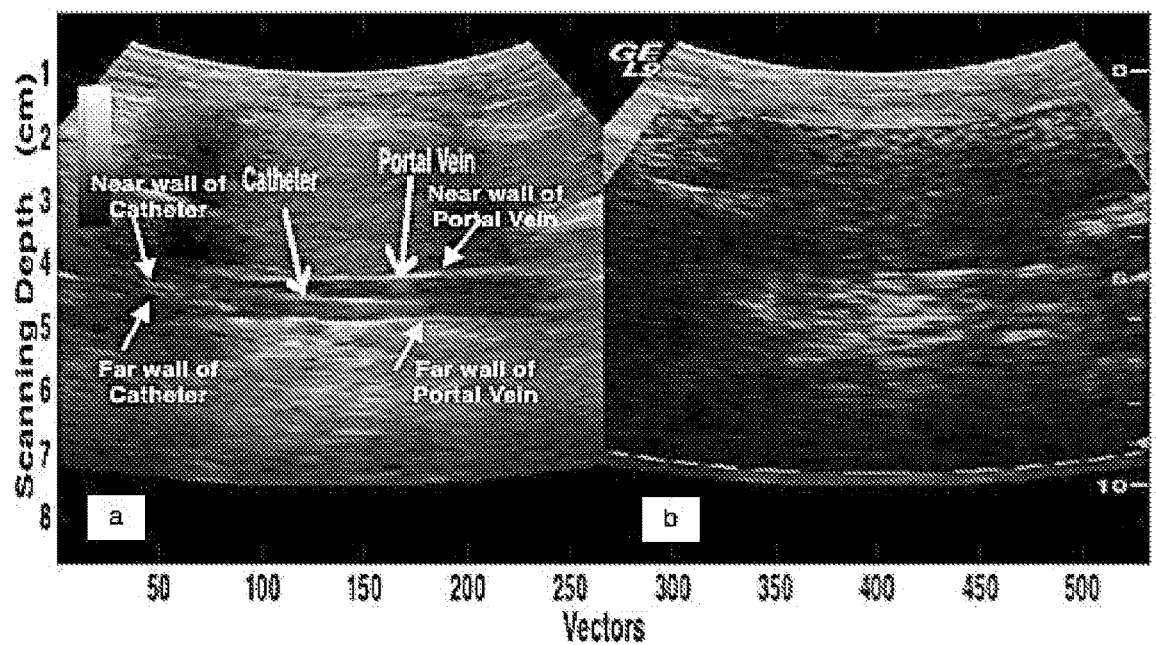
FIG. 4: [a] Dual Imaging with B mode (black and white) and SHI [b] on the left and right respectively; [c] ROI selection on the Maximum Intensity Projection of the B mode Image.
Figure 4:
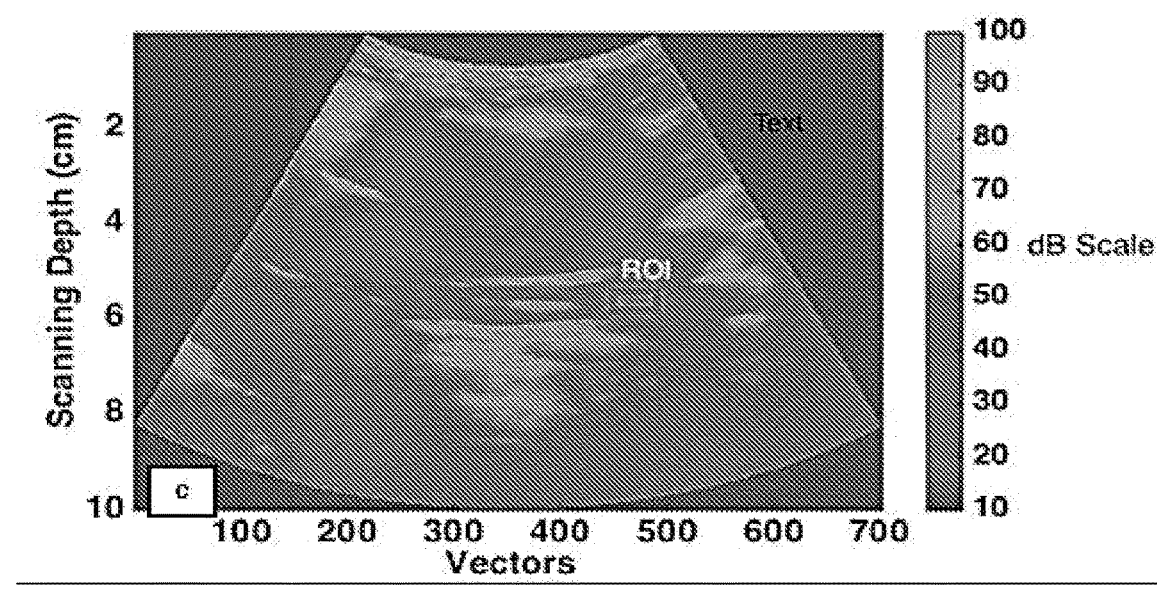

FIG. 4 shows a B mode and SHI image highlighting the portal vein and the pressure catheter along with the ROI selection on its MIP projection. The average signal over all the frames in the 0.5 MHz bandwidth around 1.25 MHz gave the subharmonic signal. The overall subharmonic amplitude in the third canine was much lower than in the other two (by about 12 dB) and too close to the noise floor to produce reasonable pressure estimates. This can be due to improper reconstitution of the agent. Hence, data from the third canine had to be excluded. The other two canines produced very similar results to those obtained in vitro. In the first canine, the pre-hypertension mean maximum subharmonic amplitude was 61.1±2.00 dB which dropped to 47.7±3.95 dB post the gelfoam injection for waveform E. Similar drops in the subharmonic amplitude for waveform E in the second canine were seen from a mean maximum subharmonic amplitude of 58.1±1.14 dB to 44.8±1.43 dB post the induction of hypertension. A reduction in subharmonic amplitude after the gelfoam injection was found to be statistically significant for all eight waveforms for the remaining two canines (p<0.01).

For the first canine, the correlation coefficient for the group of broadband waveforms was −0.80 which was significantly better than the narrowband waveforms having a correlation coefficient of −0.63. Similar results were seen for the second canine where the broadband group had a significantly better correlation of −0.83 as compared to the narrowband group having an r value of −0.32, (p<0.05). No waveform was significantly better than the other within the broadband group (p>0.05).

However, in the first canine, within the broadband group, waveform E had the highest gradient of −0.44 dB/mmHg with an r value of −0.95. Waveform G and H had a lower slope as compared to the others with G having the lowest correlation of −0.72. The values are given in Table 2 below.

TABLE 2

Slope (between the subharmonic amplitude and ambient pressure) and r values for all eight waveforms (A-H) for both canines

|  | Canine 1 | | Canine 2 | |
|---|---|---|---|---|
| Waveform | Slope (dB/mmHg) | r values | Slope (dB/mmHg) | r values |
| A | −0.25 | −0.91 | −0.01 | 0 |
| B | −0.37 | −0.84 | −0.26 | −0.92 |
| C | −0.32 | −0.91 | −0.16 | −0.85 |
| D | −0.33 | −0.92 | −0.2 | −0.98 |
| E | −0.44 | −0.95 | −0.46 | −0.96 |
| F | −0.2 | −0.98 | −0.28 | −0.85 |

TABLE 2-continued

Slope (between the subharmonic amplitude and ambient pressure) and r values for all eight waveforms (A-H) for both canines

| Waveform | Canine 1 | | Canine 2 | |
| --- | --- | --- | --- | --- |
| | Slope (dB/mmHg) | r values | Slope (dB/mmHg) | r values |
| G | −0.28 | −0.72 | −0.49 | −0.94 |
| H | −0.33 | −0.96 | −0.51 | −0.92 |

What is claimed is:

1. A method for obtaining a pressure measurement in at least one region of interest (ROI) in a subject wherein said method comprises:
    administering an amount of a microbubble ultrasound contrast agent (UCA) to said subject;
    allowing said UCA to accumulate in said subject;
    transmitting an ultrasonic wave to said ROI in said subject wherein said ultrasonic wave is a broadband wave;
    receiving an ultrasonic echo generated by reflecting the transmitted ultrasonic wave from said ROI thereby acquiring a detection signal;
    extracting a sub-harmonic component from the ultrasonic echo based on the detection signal; and
    using the inverse linear relationship between the subharmonic signal amplitude and ambient pressure to obtain said pressure measurement.

2. The method as defined in claim 1 wherein said subject is a mammal.

3. The method as defined in claim 2 wherein said mammal is a human.

4. The method as defined in claim 1 wherein said administering is intravenous.

5. The method as defined in claim 1 wherein said administering is an infusion.

6. The method as defined in claim 1 wherein said administering is a co-infusion with saline.

7. The method as defined in claim 1 wherein said UCA comprises microbubbles each of which comprises a gas enclosed by a stabilising shell.

8. The method as defined in claim 7 wherein said gas has a different compressibility compared to the blood of said subject.

9. The method as defined in claim 8 wherein said gas is a high-density, high-molecular weight gas that exhibits low solubility.

10. The method as defined in claim 9 wherein said gas is selected from the group comprising perflutren, perfluorobutane (PFB), octafluoropropane or sulfur hexafluoride.

11. The method as defined in claim 7 wherein said stabilising shell comprises a protein, lipid or polymer.

12. The method as defined in claim 11 wherein said stabilising shell comprises a protein.

13. The method as defined in claim 12 wherein said protein is albumin.

14. The method as defined in claim 7 wherein said stabilising shell comprises a lipid.

15. The method as defined in claim 14 wherein said lipid is a phospholipid.

16. The method as defined in claim 15 wherein said phospholipid is phosphatidyl serine (PS).

17. The method as defined in claim 15 wherein said phospholipid is hydrogenated egg phosphatidyl serine (HEPS).

18. The method as defined in claim 11 wherein said stabilising shell comprises a polymer.

19. The method as defined in claim 18 wherein said polymer is an aliphatic polyester based on lactic acid (PLA) and lactic/glycolic acid (PLGA).

20. The method as defined in claim 18 wherein said polymer is alginate.

21. The method as defined in claim 1 wherein said ultrasonic wave is a Gaussian windowed pulse.

22. The method as defined in claim 21 wherein said Gaussian windowed pulse is selected from the group comprising a Gaussian windowed square wave, a Gaussian windowed binomial filtered square wave, a Gaussian windowed binomial filtered square 90° shift wave.

23. The method as defined in claim 1 wherein said ultrasonic wave is a chirp pulse.

24. The method as defined in claim 1 wherein said ROI comprises the portal vein of said subject.

25. The method as defined in claim 24 wherein said ROI further comprises the hepatic vein of said subject.

26. The method as defined in claim 1 wherein said ROI comprises a heart cavity of said subject.

27. The method as defined in claim 26 wherein said heart cavity is a ventricle.

28. The method as defined in claim 27 wherein said ventricle is the left ventricle.

29. The method as defined in claim 1 wherein said ROI comprises a diseased tissue in said subject.

30. The method as defined in claim 29 wherein said diseased tissue is one selected from the group comprising a malignant tumour and an atherosclerotic plaque.

31. The method as defined in claim 29 wherein ROI said further comprises non-diseased tissue in said subject.

* * * * *